United States Patent [19]

Haber et al.

[11] Patent Number: 4,947,863
[45] Date of Patent: Aug. 14, 1990

[54] ENERGY-DISSIPATING, SAFETY BLOOD COLLECTION TUBE HOLDER

[75] Inventors: Terry M. Haber; Clark B. Foster, both of El Toro; William H. Smedley, Lake Elsinore, all of Calif.

[73] Assignee: Habley Medical Technology Corporation, Laguna Hills, Calif.

[21] Appl. No.: 238,119

[22] Filed: Aug. 30, 1988

[51] Int. Cl.$^5$ .............................................. A61B 5/14
[52] U.S. Cl. .................................. 128/764; 604/110; 604/198; 604/263
[58] Field of Search ............... 128/763, 764, 765, 766; 604/198, 263, 196, 197, 110

[56] References Cited

U.S. PATENT DOCUMENTS

| | | | |
|---|---|---|---|
| 2,880,725 | 4/1959 | Kendall | 604/196 |
| 4,166,450 | 9/1979 | Abramson | 128/764 |
| 4,409,990 | 10/1983 | Mileikowsky | 128/763 |
| 4,631,057 | 12/1986 | Mitchell | 604/198 |
| 4,737,144 | 4/1988 | Choksi | 604/198 |
| 4,758,231 | 7/1988 | Haber et al. | 604/198 |
| 4,774,964 | 10/1988 | Bonaldo | 128/763 |
| 4,790,827 | 12/1988 | Haber et al. | 604/198 |

Primary Examiner—Kyle L. Howell
Assistant Examiner—K. M. Pfaffle
Attorney, Agent, or Firm—Morland C. Fischer

[57] ABSTRACT

A disposable blood collection tube holder having particular application to the field of vacuum tube phlebotomy and being characterized by maximum safety and the ability to avoid an accidental needle stick and the spread of a contagious, and possibly life threatening, disease. The blood collection tube holder comprises an inner cylinder, from which a double ended hypodermic needle cannula is supported, and an outer protective sleeve. The outer sleeve is coaxially aligned with and slideable axially over the inner cylinder from a retracted position, at which the needle cannula is exposed for making a veni puncture and drawing a blood sample, to an extended position, at which the cannula is completely surrounded by and rendered irretrievable within the outer sleeve. A plurality of successive energy absorbing and force dissipating stations are located along the inner cylinder. The multiple stations cooperate with a segmented ring which extends around the periphery of the outer sleeve to perform the dual functions of locking the outer sleeve in the axially extended position while, at the same time, transforming the jarring impact locking forces into relatively smooth deceleration forces, so as to avoid a whiplash of the needle cannula and a possible splattering of a blood sample.

22 Claims, 2 Drawing Sheets

ENERGY-DISSIPATING, SAFETY BLOOD COLLECTION TUBE HOLDER

BACKGROUND OF THE INVENTION

1. Field of the Invention

This invention relates to a disposable blood collection tube holder having particular application to the field of vacuum tube phlebotomy and means by which to safely and reliably shield an associated hypodermic needle cannula after use so as to prevent both an accidental needle stick and the possible splattering of a disease laden blood sample as a consequence of cannula whiplash.

2. Prior Art

The heightened awareness of the need for infection control, while drawing samples from blood-precautionary patients, has inspired the design of many safety blood collection tube holders which employ a needle shielding means so as to reduce the probability of an accidental needle stick by a contaminated needle cannula and by nosocomial infection of lethal viruses and other microorganisms. By way of example, devices are known which include a sliding outer protective sleeve which is advanceable axially over an inner cylinder to surround and shield a contaminated hypodermic needle, after use. However, a problem commonly suffered by these conventional devices is their tendency to splatter microdroplets of a patient's blood, both inside and outside of the outer sleeve, when said outer sleeve is advanced to and locked in its forward-most shielding position.

More particularly, every needle cannula has its own characteristic frequency response by which it may be susceptable to whiplash through either sympathetic vibration or imposed impact loads. Such vibrations and loads are frequently generated by the jarring impact forces associated with advancing and locking the outer sleeve in its forward-most position relative to the inner cylinder. As a consequence of these impact locking forces and the corresponding needle whiplash, the possibility of splattering a disease laden blood sample still exists, even though the cannula is completely surrounded and shielded.

An example of a shielded blood collection tube holder to which the present invention is applicable may be found by referring to U.S. Pat. No. 4,758,231 issued July 19, 1988, which patent has been assigned to the assignee of this patent application.

SUMMARY OF THE INVENTION

In general terms, a disposable blood collection tube holder is disclosed having particular application to the field of vacuum tube phlebotomy. The blood collection tube holder comprises an inner cylinder, from which a double ended hypodermic needle cannula is supported, and an outer protective sleeve which is coaxially aligned with and axially advanceable over the inner cylinder. That is, the outer sleeve may be moved from a retracted position, at which one end of the needle cannula is exposed for making a veni puncture and drawing a blood sample, to an axially extended position, at which the needle cannula is completely surrounded and shielded by the outer sleeve to permit a safe handling of the device while avoiding an accidental needle stick and the possible spread of a contagious disease. The outer sleeve is locked in the axially extended position to form a disposal package which prevents access to and reuse of the needle cannula.

In accordance with the present invention, a multiple stage, shock absorbing system is disclosed which includes overlapping and increasingly resistant deceleration stations to absorb and dampen the vibrations and loads that are generated by jarring impact forces when the outer sleeve is advanced and locked in the axially extended position. Thus, a whiplash of the needle cannula is prevented and the possibility of splattering a disease laden blood sample is avoided.

More particularly, the inner cylinder includes a plurality of resilient fingers which are interspersed between a corresponding plurality of rigid columns. The fingers are biased so as to be rotated into the interior of the inner cylinder through respective windows. Each window is defined by an arcuate, energy dissipating shoulder. Each of the resilient fingers and rigid columns includes a respective decelerating ramp portion. A segmented ring extends around the periphery of the outer sleeve and includes a plurality of inclined egdes that cooperate with the decelerating ramp portions of the fingers and columns.

In operation, when the outer sleeve is advanced relative to the inner cylinder towards the axially extended position, the inclined edges of the segmented ring of the outer sleeve initially contact respective ones of the decelerating ramp portions of the resilient fingers and rigid columns of the inner cylinder. Accordingly, the resilient fingers of the inner cylinder are stressed and rotated, at a first decelerating stage, in a radially inward direction through respective windows. Moreover, the segmented ring of the outer sleeve is stressed, at a second decelerating stage, in a radially outward direction. After the inclined edges of the segmented ring travel up and across the resilient fingers, each of said inclined edges slides gently through a window of the inner cylinder to be received between a resilient finger and an energy dissipating shoulder, whereby to lock the outer sleeve in the axially extended position. What is more, the inclined edges of the outer sleeve contact the energy dissipating shoulders of the inner cylinder, at a third decelerating stage. The result of the foregoing multiple stage shock absorbing system is to sequentially and collectively transform the otherwise jarring impacting locking forces into a relatively smooth deceleration force which avoids needle cannula whiplash and the possible splattering of a disease laden blood sample.

DESCRIPTION OF THE PREFERRED EMBODIMENT

Figure 1:
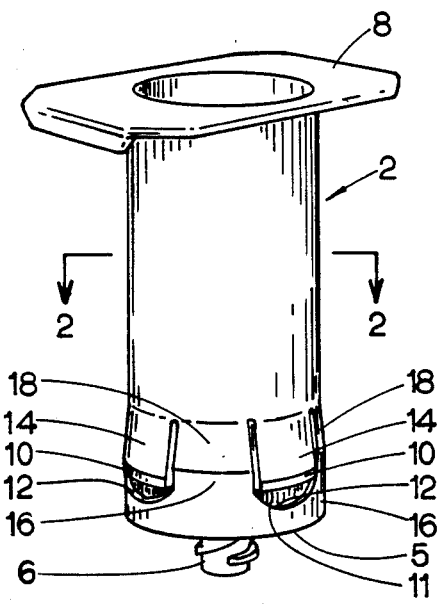
FIG. 1 is a perspective illustration of the inner cylinder which forms the safety blood collection tube holder of the present invention.
Figure 2:
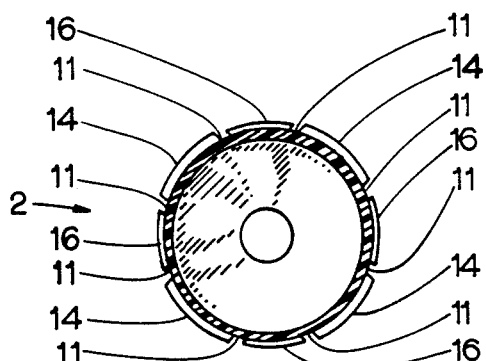
FIG. 2 is a cross-section taken along lines 2—2 of FIG. 1.
Figure 3:
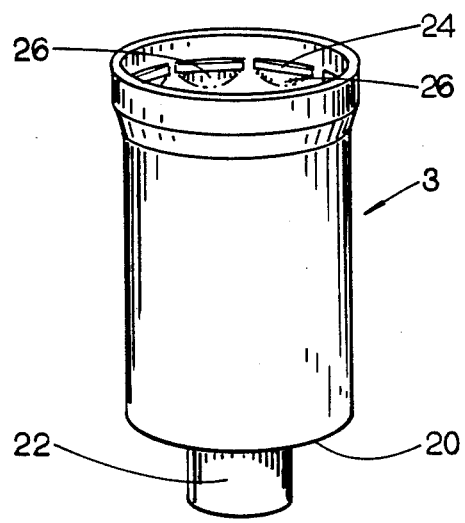
FIG. 3 is a perspective view of the outer protective sleeve which also forms the safety blood collection tube holder of the present invention.

The disposable blood collection tube holder which forms the present invention is best described while referring to the drawings, where FIGS. 1 and 2 are illustrative of an inner cylinder 2, and FIG. 3 is illustrative of an outer protective sleeve 3. As will be described in greater detail hereinafter, when referring to FIGS. 4 and 5, the outer sleeve 3 is adapted to receive therewithin and slide axially over the inner cylinder 2 from a retracted position (at which a hypodermic needle cannula is exposed to make a veni puncture for the purpose of drawing a blood sample) to an extended position (at which the needle cannula is completely surrounded and safely shielded by the outer sleeve for the purpose of preventing an accidental needle stick). Thus, it may be appreciated that the presently disclosed blood collection tube holder has particular application to the field of vacuum tube phlebotomy where one or more samples of a patient's blood may be successively drawn into respective blood collection tubes.

Referring initially to FIGS. 1 and 2, the hollow inner cylinder 2 is shown having an open proximal end and a substantially closed distal end wall 5. A relatively narrow neck 6 having an external screw thread extends outwardly from an opening in the distal end wall 5. A flange 8 surrounds the open proximal end of cylinder 2 to improve the handling of the blood collection tube holder and the manipulation of the inner cylinder 2 and outer sleeve 3 relative to one another.

A plurality of (e.g. four) resilient fingers 10 are evenly spaced around the periphery of inner cylinder 2. According to a preferred embodiment, areas or windows 11 are cut out from the inner cylinder 2 above the distal end wall 5 thereof to form the resilient fingers 10. The resilient fingers 10 are cantilevered at one end and adapted to pivot at their opposite end inwardly into the inner cylinder 2 through respective windows 11 for an important shock absorbing purpose that will soon be described. More particularly, the windows 11 surround resilient fingers 10 and define arcuate-shaped energy dissipating shoulders 12 which are axially aligned with and spaced distally from respective ones of said fingers 10. Each resilient fingers 10 includes a decelerating ramp portion 14 which slopes upwardly and distally thereover so as to bias the fingers 10 to be pivoted inwardly of the inner cylinder 2, via windows 11, when the outer sleeve 3 slides axially thereover.

Interspersed between the plurality of resilient, pivotable fingers 10 is a corresponding plurality of (e.g. four) rigid and continuous columns 16. Each column 16 includes a decelerate ramp portion 18 which slopes upwardly and distally thereover. The respective decelerating ramp portions 14 and 18 of fingers 10 and columns 16 are arranged in spaced parallel alignment with one another. Moreover, the shapes of the respective ramp portions 14 and 18 are generally identical to one another.

Referring now to FIG. 3, the outer protective sleeve 3 is shown comprising a generally hollow, cylindrical body having an open proximal end and a substantially closed distal end wall 20. A neck 22 having an internal screw thread extends outwardly from an opening in the distal end wall 20. The screw threaded neck 22 of outer sleeve 3 is sized to surround and be rotated into mating engagement with the screw threaded neck 6 of inner cylinder 2 so as to releasably attach the inner cylinder 2 and outer sleeve 3 together when said cylinder and sleeve are disposed in the retracted position (of FIG. 4). Extending around the periphery of outer sleeve 3 below the proximal end thereof is an inner segmented ring 24. Segmented ring 24 comprises a plurality of uniformly spaced, radially inward projecting inclined edges 26 which are sized and shaped so as to cooperate with respective ones of the decelerating ramp portions 14 and 18 of the inner cylinder 2 (of FIG. 1) when the outer sleeve 3 slides over the inner cylinder 2 from the retracted to the axially extended position. While it is preferable that inner ring 24 be comprised of a plurality of spaced, inclined edges 26, as shown in FIG. 3, it is to be understood that inner ring 24 could also be formed as a continuous, radially inward projecting lip, ramp, or other similar configuration by which to assure a reliable and simultaneous contact with the ramp portions 14 and 18 of inner cylinder 2.

Figure 4:
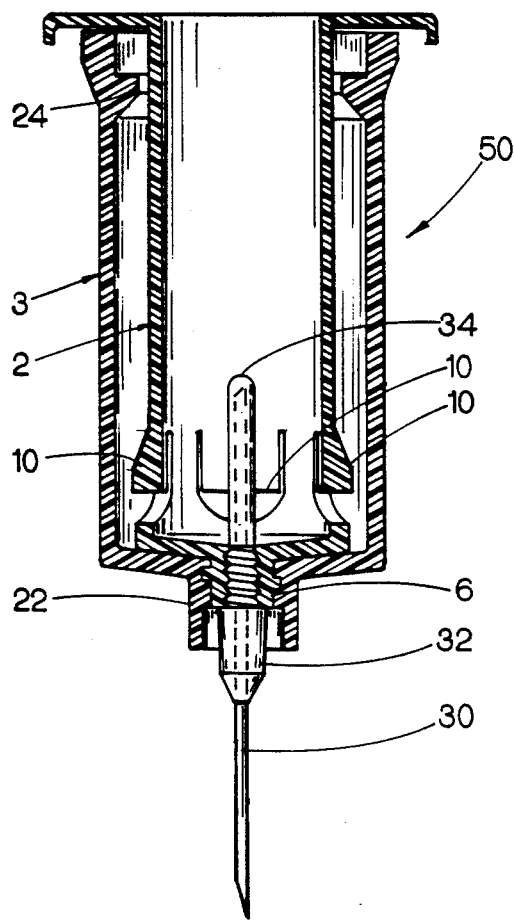
FIG. 4 is a cross-section of the safety blood collection tube holder of the present invention with the inner cylinder and outer sleeve retained in the retracted position relative to one another.

FIG. 4 of the drawings shows the blood collection tube holder 50 of the present invention in the assembled configuration with the outer protective sleeve 3 coaxially aligned with and disposed in the retracted position relative to the inner cylinder 2, such that the segmented ring 24 of outer sleeve 3 is located proximally and out of contact with the resilient fingers 10 of inner cylinder 2. Moreover, the respective necks 6 and 22 of inner cylinder 2 and outer sleeve 3 are mated together. A conventional double ended hypodermic needle cannula 30 is also shown being retained at the distal end of inner cylinder 2. More particularly, the needle cannula 30 is carried by a screw threaded hub 32. The needle hub 32 is adapted to be screwed into engagement with the neck 6 of inner cylinder 2, such that one end of cannula 30 projects outwardly and distally from cylinder 2, and the opposite end of cannula 30 project proximally into the interior of cylinder 2. A soft rubber sheath 34 typically covers the proximal end of cannula 30 to avoid contamination thereof.

In the retracted position of FIG. 3, the distal end of needle cannula 30 is exposed for penetrating a targeted tissue area of the patient and thereby making a veni puncture. A conventional evacuated blood collection phlebotomy tube (not shown) is moved through the open proximal end of the inner cylinder 2 until the proximal end of needle cannula 30 communicates with said blood collection tube (through a rubber stopper) at the interior of cylinder 2. A sample of the patient's blood may then be automatically suctioned via cannula 30 until the blood collection tube is filled.

When the last blood sample has been taken, the needle cannula 30 is withdrawn from the patient and the blood collection tube is removed through the open proximal end of inner cylinder 2. In order to prevent an accidental needle stick and the spread of a contagious, and possible life threatening, disease, the previously interconnected necks 6 and 22 of the inner cylinder 2 and outer sleeve 3 are rotated out of engagement with one another, and the outer sleeve 3 is advanced distally relative to the inner cylinder 2 from the retracted position of FIG. 4 to the axially extended position of FIG. 5. That is to say, the inner cylinder 2 is grasped below the flange 8 and the outer sleeve 3 is advanced axially and distally thereover.

Figure 5:
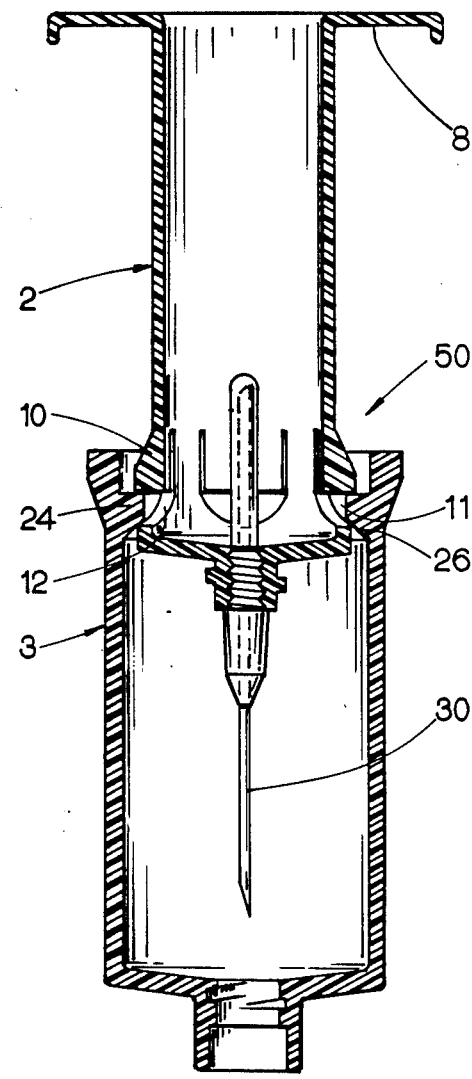
FIG. 5 is a cross-section of the safety blood collection tube holder with the outer sleeve advanced to the axially extended position relative inner cylinder.
Figure 6:
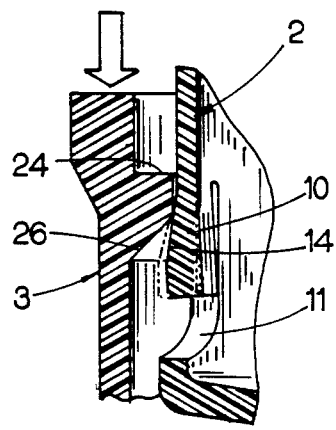
FIGS. 6–8 illustrate the three successive energy absorbing and force dissipating stations by which relatively harsh impact locking forces are transformed into relatively smooth deceleration forces.

Referring now to FIGS. 5-8 of the drawings, the continued axial advancement of outer sleeve 3 over inner cylinder 2 correspondingly moves some of the radially projecting inclined edges 26 of the segmented ring 24 of outer sleeve 3 into simultaneous and oblique contact with each of the decelerating ramp portions 14 of the resilient fingers 10 of inner cylinder 2 (best shown in FIG. 6). As is also best shown in FIG. 6, the movement of edges 26 up the decelerating ramp portions 14 causes the plurality of resilient fingers 10 to be stressed and rotated in a radially inward direction into the inner cylinder 2 (represented in phantom) via windows 11. The contact of decelerating ramp portions 14 by segmented ring 24 and the resulting rotation of resilient fingers 10 through windows 11, as illustrated in FIG. 6, establish a first energy absorbing stage for decelerating the displacement of outer sleeve 3 relative to inner cylinder 2.

Figure 7:
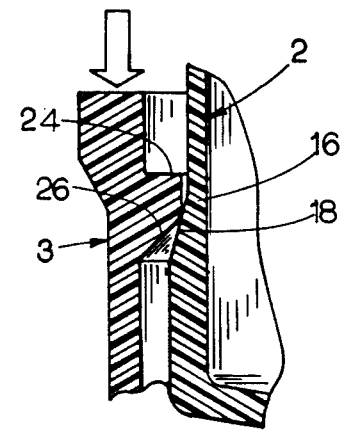

At approximately the same time that some of the radially projecting inclined edges 26 of inner segmented ring 24 engages the decelerating ramp portions 14 of resilient fingers 10, and referring now to FIG. 7 of the drawings, the remaining inclined edges 26 of the segmented ring 24 of outer sleeve 3 obliquely and simultaneously contact each of the decelerating ramp portions 18 of the rigid columns 16 of inner cylinder 2. The movement of edges 26 up the rigid decelerating ramp portions 18, which ramp portions are interspersed between the resilient fingers 10, stresses the edges 26 (and the proximal end of outer sleeve 3) in a radially outward direction, whereby to establish a second energy absorbing stage for decelerating the displacement of outer sleeve 3 relative to inner cylinder 2.

Figure 8:
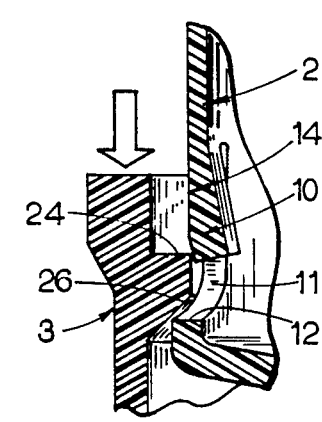

The further axial and distal advancement of outer sleeve 3 relative to inner cylinder 2, as shown in FIG. 8 of the drawings, causes the inclined edges 26 of the segmented ring 24 of outer sleeve 3 to move up and completely across the decelerating ramp portions 14 of the resilient fingers 10 which have previously been rotated into inner cylinder 2 via windows 11. Accordingly, the inclined edges 26 slide behind fingers 10 and fall gently, with minimal shock impact, into the windows 11, such that said edges 26 contact the arcuate-shaped, energy dissipating shoulders 12. The engagement of the arcuate (i.e. non-linear) shoulders 12 by inclined edges 26 establishes a third energy absorbing stage for further decelerating the displacement of the outer sleeve 3 relative to inner cylinder 2.

The resilient fingers 10 of inner cylinder 2, which were formally contacted by the inclined edges 26 of outer sleeve 3, are now free to automatically rotate away from the interior of inner cylinder 2 and return to their pre-stressed configuration. Hence, and is best shown in FIG. 5, the outer sleeve 3 of blood collection tube holder 50 is locked in the axially extended position with the edges 26 of segmented ring 24 received and retained within windows 11 between fingers 10 and shoulders 12. Thus, a positive self-locking feature is provided, whereby to prevent the continued axial and distal advancement of outer sleeve 3 over inner cylinder 2 as well as a return of the outer sleeve to the retracted position (of FIG. 4). Moreover, a disposal cartridge is created (in FIG. 5) having the inner cylinder 2 and outer sleeve 3 locked in the axially extended position relative to one another with the needle cannula 30 surrounded, shielded, and rendered irretrievable and unusable therewithin, so as to permit a safe handling and disposal of blood collection tube holder 50 while avoiding an accidental needle stick and the possibility of transmitting a contagious and life threatening disease.

What is more, and in accordance with an important advantage of the present invention, the outer sleeve 3 is securely and reliably locked in the axially extended position of FIG. 5 in a manner which absorbs and/or dampens the harsh locking forces and thereby prevents the associated shock from causing the needle cannula 30 to whiplash and, possibly, splatter the patient's blood. That is to say, the three previously described decelerating and energy absorbing stages sequentially and collectively transform the otherwise jarring impact locking forces into relatively smooth deceleration forces. Accordingly, the blood collection tube holder 50 is characterized by maximum safety and reliability by preventing an accidental needle stick and controlling the spread of infection and disease.

It will be apparent that while a preferred embodiment of the present invention has been shown and described, various modifications and changes may be made without departing from the true spirit and scope of the invention. For example, although the blood collection tube holder 50 has been described in the specification as having paticular application to the field of vacumm tube phlebotomy, it is to be expressly understood that the safety and energy absorbing features of this invention are also applicable to a syringe having a single ended needle cannula for expulsing medication to a patient from a fluid filled syringe cylinder. In this case, however, it may be desirable to relocate the decelerating ramp portions 14 and 18 at the outer sleeve and the segmented ring 24 around the periphery of the inner cylinder.

Having thus set forth the preferred embodiment of the invention, what is claimed is:

1. A shielded syringe comprising:
    a hollow inner cylinder having proximal and distal ends;
    a hypodermic needle cannula supported at and extending outwardly from the distal end of said inner cylinder, said cannula also communicating with the interior of said inner cylinder;
    an outer protective sleeve having an open proximal end and an opening in a substantially closed distal end, said outer sleeve being coaxially aligned with and axially advanceable relative to said inner cylinder from a retracted position, where said cannula projects outwardly through the opening in the distal end of said outer sleeve for penetrating the tissue of a patient, to an extended position, where said cannula is surrounded and shielded by said sleeve;
    means for locking said outer sleeve in the axially extended position relative to said inner cylinder; and
    means for decelerating said outer sleeve and damping the locking forces generated when said sleeve is advanced to and locked in the axially extended position, so as to prevent needle cannula whiplash and the possible splattering of the patient's blood, said decelerating and damping means including first surface means extending from said inner cylinder and first radial projection means extending from said outer sleeve, said first surface means being pivotally attached to said inner cylinder so as to be engaged and rotated into the hollow interior of said inner cylinder by the first radial projection means of said outer sleeve when said sleeve is advanced to the axially extended position.

2. The syringe recited in claim 1, wherein said needle cannula is double ended, one end of said cannula projecting outwardly from said inner cylinder for making a veni puncture and the opposite end of said cannula projecting into the interior of said inner cylinder.

3. The syringe recited in claim 1, wherein said first surface means includes a plurality of ramps extending outwardly from and pivotally attached to said inner cylinder, and said first radial projection means includes a plurality of inclined edges extending inwardly from said outer sleeve, certain ones of said plurality of inclined edges engaging respective ones of said plurality of ramps for rotating said ramps into the interior of said cylinder when said outer sleeve is advanced to the axially extended position.

4. The syringe recited in claim 3, wherein said plurality of pivotal ramps are arranged in spaced, parallel alignment with one another around said inner cylinder, and said plurality of inclined edges are arranged in spaced, parallel alignment with one another around said outer sleeve.

5. The syringe recited in claim 3, further comprising a plurality of windows formed in said inner cylinder to surround respective ones of said plurality of pivotal ramps, said pivotal ramps being rotated into the interior of said inner cylinder via said windows when the inclined edges of said outer sleeve engage said pivotal ramps as said outer sleeve is advanced to the axially extended position.

6. The syringe recited in claim 5, wherein said plurality of windows of said inner cylinder are sized to receive the plurality of inclined edges of said outer sleeve therethrough after said inclined edges engage and travel over said pivotal ramps as said outer sleeve is advanced to the axially extended position, the receipt of said inclined edges within said windows forming said means for locking said outer sleeve in the axially extended position relative to said inner cylinder.

7. The syringe recited in claim 6, wherein each of said plurality of windows has a respective arcuate-shaped end, the plurality of inclined edges of said outer sleeve travelling over the plurality of pivotal ramps of said inner cylinder for receipt through said plurality of windows thereof and engagement with respective ones of said arcuate-shaped window ends when said outer sleeve is advanced to the axially extended position, the engagement of said window ends by said inclined edges also forming said decelerating and damping means.

8. The syringe recited in claim 1, wherein said decelerating and damping means further includes second surface means extending from said inner cylinder and second radial projection means extending from said outer sleeve, the second surface means being fixedly attached to said inner cylinder so as to be engaged by the second radial projection means of said outer sleeve to thereby apply a radially directed stress to said outer sleeve when said sleeve is advanced to the axially extended position.

9. The syringe recited in claim 8, wherein said second surface means includes a plurality of ramps extending outwardly from and fixedly attached to said inner cylinder, and said second radial projection means includes a plurality of inclined edges extending inwardly from said outer sleeve, certain ones of said plurality of inclined edges engaging respective ones of said plurality of ramps for applying a radially outward directed stress to said outer sleeve when said sleeve is advanced to the axially extended position.

10. The syringe recited in claim 9, wherein said plurality of fixedly attached ramps are arranged in spaced, parallel alignment with one another around said inner cylinder, and said plurality of inclined edges are arranged in spaced parallel alignment with one another around said outer sleeve.

11. A shielded syringe comprising:
an inner cylinder having a hollow interior and proximal and distal ends;
a hypodermic needle cannula supported at and extending outwardly from the distal end of said inner cylinder, said cannula communicating with the interior of said inner cylinder;
an outer protective sleeve having an open proximal end and an opening in a substantially closed distal end, said outer sleeve being coaxially aligned with and axially advanceable relative to said inner cylinder from a retracted position, where said cannula projects outwardly through the opening in the distal end of said outer sleeve for penetrating the tissue of a patient, to an extended position, where said cannula is surrounded and shielded by said sleeve;
first ramp means pivotally attached to said inner cylinder and rotatable inwardly thereof; and
first radial projection means extending from said outer sleeve,
the ramp means of said inner cylinder being engaged by the radial projection means of said outer sleeve so as to rotate said ramp means into the hollow interior of said cylinder and thereby decelerate said outer sleeve as said sleeve is advanced to the axially extended position.

12. The syringe recited in claim 11, wherein said needle cannula is double ended, one end of said cannula projecting outwardly from said inner cylinder for making a veni puncture and the oposite end of said cannula projecting into the interior of said inner cylinder.

13. The syringe recited in claim 11, wherein said first ramp means includes a plurality of ramps pivotally attached to and extending outwardly from said inner cylinder, and said first radial projection means includes a plurality of projections extending inwardly from said outer sleeve, certain ones of said plurality of radial projections engaging respective ones of said pivotal ramps for rotating said ramps inwardly of said cylinder when said outer sleeve is advanced to the axially extended position.

14. The syringe recited in claim 13, wherein said plurality of pivotal ramps are arranged in spaced, parallel alignment with one another around the periphery of said inner cylinder, and said plurality of radial projections are arranged is spaced, parallel alignment with one onother around the periphery of said outer sleeve.

15. The syringe recited in claim 13, further comprising a plurality of windows formed in said inner cylinder to surround respective ones of said plurality of pivotal ramps, said pivotal ramps being rotated into the interior of said inner cylinder via said windows when the radial projections of said outer sleeve engage said pivotal ramps as said outer sleeve is advanced to the axially extended position.

16. The syringe recited in claim 15, wherein said plurality of windows of said inner cylinder are sized to receive the plurality of radial projections of said outer sleeve therethrough after said radial projections engage and travel over said pivotal ramps as said outer sleeve is advanced to the axially extended position, the receipt of said radial projections within said windows forming means for locking said outer sleeve in the axially extended position relative to said inner cylinder.

17. The syringe recited in claim 16, wherein each of said plurality of windows has a respective arcuate-shaped end, the plurality of radial projections of said outer sleeve travelling over the plurality of pivotal ramps of said inner cylinder for receipt through said plurality of windows thereof and engagement with respective ones of said arcuate-shaped window ends for further decelerating said outer sleeve when said sleeve is advanced to the axially extended position.

18. The syringe recited in claim 11, further comprising second ramp means fixedly attached to said inner cylinder, and second radial projection means extending from said outer sleeve, the second ramp means of said inner cylinder being engaged by the second radial projection means of said outer sleeve so as to apply a radially outward directed stress to said outer sleeve for further decelerating said outer sleeve when said sleeve is advanced to the axially extended position.

19. The syringe recited in claim 18, wherein said second ramp means includes a plurality of ramps extending outwardly from and fixedly attached to said inner cylinder, and said second radial projection means includes a plurality of radial projections extending inwardly from said outer sleeve, certain ones of said plurality of radial projections engaging respective ones of said plurality of ramps for applying the radially outward directed stress to said outer sleeve when said sleeve is advanced to the axially extended position.

20. The syringe recited in claim 19, wherein said plurality of fixedly attached ramps are arranged is spaced, parallel alignment with one another around said inner cylinder, and said plurality of radial projections are arranged in spaced, parallel alignment with one another around said outer sleeve.

21. A shielded blood collection tube holder including an inner syringe cylinder having a hollow interior, an open proximal end and a substantially closed distal end, a double ended hypodermic needle cannula supported at and extending both inwardly and outwardly from said distal end, and an outer protective sleeve having an open proximal end and opening in a substantially closed distal end, said outer sleeve coaxially aligned with and axially advanceable relative to said inner cylinder from a retracted position, where said needle cannula projects through the opening in said sleeve, to an extended position, were said needle cannula is located within and completely surrounded by said sleeve, said blood collection tube holder comprising:

a first ramp pivotally attached to said inner cylinder so as to be rotatable into the hollow interior thereof;

a second ramp fixedly attached to said inner cylinder; and first and second radial projections extending from said outer sleeve, said first and second ramps of said inner cylinder being respectively engaged by said first and second radial projections of said outer sleeve such that said first radial projection rotates said first ramp into the interior of said cylinder and said second ramp applies a radially outward stress to the second radial projection of said outer sleeve to thereby decelerate said outer sleeve when said sleeve is advanced to the axially extended position.

22. The blood collection tube holder recited in claim 21, wherein said first and second ramps are arranged in parallel alignment with one another around the periphery of said inner cylinder and said first and second radial projections are arranged in parallel alignment with one another around the periphery of said outer sleeve.

* * * * *